United States Patent [19]

De Luca et al.

[11] Patent Number: 4,595,598
[45] Date of Patent: Jun. 17, 1986

[54] CRYSTALLINE ALUMINA COMPOSITES

[75] Inventors: Robert D. De Luca, Pennington; Robin M. Forbes-Jones, Titusville, both of N.J.

[73] Assignee: Johnson & Johnson Dental Products Company, East Windsor, N.J.

[21] Appl. No.: 602,874

[22] Filed: Apr. 23, 1984

[51] Int. Cl.[4] .......................... A01N 1/02; A61C 3/00
[52] U.S. Cl. .................................... 427/2; 427/407.1; 427/419.2; 428/689; 433/8; 433/9; 433/199.1
[58] Field of Search ............... 433/199, 8, 9; 428/688, 428/689, 447, 448, 451; 427/2, 407.1, 419.2

[56] References Cited

U.S. PATENT DOCUMENTS 3,625,740 12/1971 Hurley .............................. 427/299
3,764,507 10/1973 McKinnon et al. ............ 317/234 R Primary Examiner—Lorenzo B. Hayes
Attorney, Agent, or Firm—Charles J. Metz

[57] ABSTRACT

The adhesion of crystalline alumina to adhesives is enhanced by coating the surface of the alumina that is to be in contact with the adhesive, with a very thin coating of a siliceous material such as sputter coated silica.

19 Claims, 15 Drawing Figures

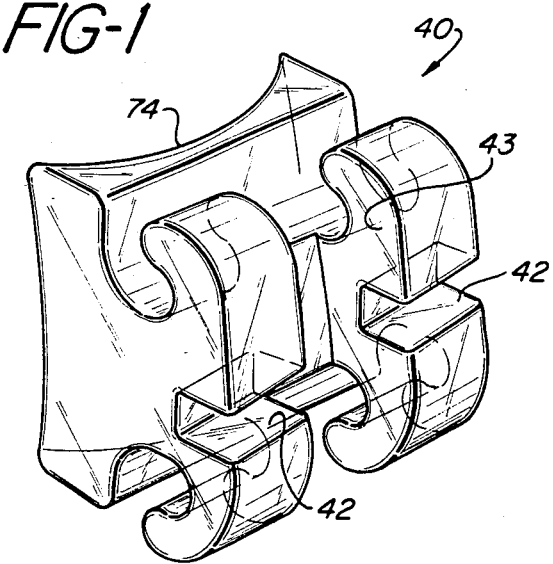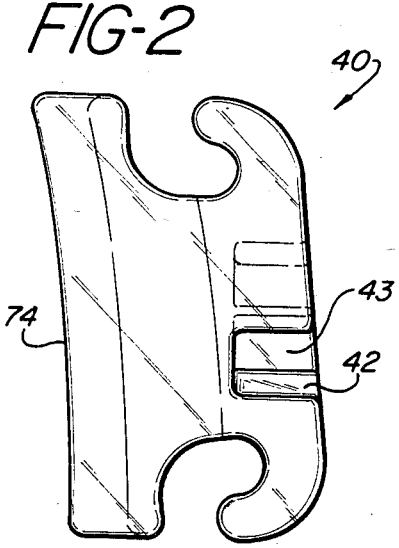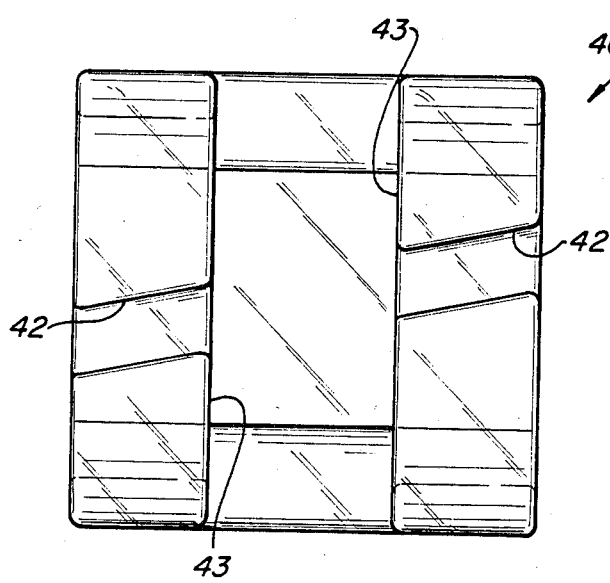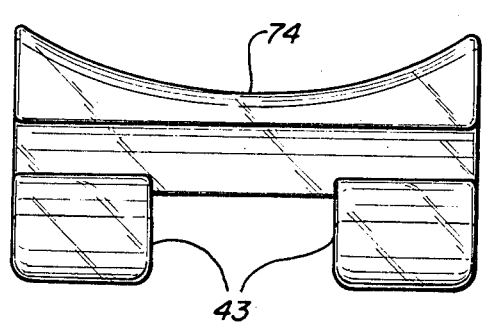

4,595,598

CRYSTALLINE ALUMINA COMPOSITES

The invention relates to composites comprising crystalline alumina bonded to a substrate, and to a method for making such composites.

BACKGROUND OF THE INVENTION

In application Ser. No. 602,876, now abandoned, for "Crystalline Alumina Orthodontic Bracket", filed on the same day as this application and assigned to the same assignee as this application, there is disclosed orthodontic brackets comprising as a load bearing member crystalline alumina. As is disclosed in said application, one of the problems inherent in the use of crystalline alumina orthodontic brackets is bonding them to teeth (or to any other substrate) because of the high surface energy of crystalline alumina.

This invention relates to one means for enhancing the bond of crystalline alumina to substrates. While the invention is described chiefly in terms of its use in connection with orthodontic brackets, the invention is applicable to the bonding of crystalline alumina articles to any substrate.

BRIEF SUMMARY OF THE INVENTION

The invention provides composites comprising crystalline alumina adhesively bonded (i.e., by using an adhesive) to a substrate, wherein at least a portion of the surface of the alumina that is bonded to said substrate has a thin, adherent siliceous coating, said coating forming a strong adhesive bond to the adhesive bonding the crystalline alumina to the substrate. The invention also provides a method of producing a composite which comprises coating at least a portion of a surface of a crystalline alumina article with a thin, adherent coating of a siliceous material, and then bonding the resultant coated surface to a substrate with an adhesive that forms a strong adhesive bond to said siliceous material.

THE PRIOR ART

The semi-conductor art has disclosed articles made of single crystal alumina having a coating of silica. For instance, see McKinnon et al., U.S. Pat. No. 3,764,507.

Hurley, in U.S. Pat. No. 3,625,740, discloses a process for treating sapphire surface with a silane to enhance adhesion to an epoxy resin.

BRIEF DESCRIPTION OF THE DRAWINGS

FIG. 1 is a perspective view of an orthodontic bracket made of crystalline alpha-alumina;

FIG. 2 is a side view of the bracket of FIG. 1;

FIG. 3 is a front view of the bracket of FIG. 1;

FIG. 4 is a top view of the bracket of FIG. 1;

DETAILED DESCRIPTION OF THE INVENTION

As was mentioned above, the invention will be described in terms of bonding crystalline alumina, preferably crystalline alpha-alumina, orthodontic brackets to substrates, including teeth, although it is applicable to other crystalline alumina articles.

As used herein, the term "crystalline alumina" is intended to include only essentially monocrystalline alumina, that is, alumina comprised of a single crystal or two or more single crystals grown together longitudinally but separated by a relatively small angle (usually within 4°, determined with respect to the C-axes of the neighboring single crystals) grain boundary.

Preferably, the orthodontic bracket is entirely crystalline alpha-alumina. Such a bracket can be produced by first drawing a crystalline alpha-alumina rod from a melt, wherein the rod has a predetermined cross-sectional configuration, by slicing the rod into individual blanks, and then machining the blanks to produce the bracket. A detailed description of this process follows.

The preferred procedure for producing a crystalline alpha-alumina rod having predetermined cross-sectional configuration is the EFG (for Edge-defined, Film-fed, Growth) modification of the Czochralski process for growing crystalline alpha-alumina. The EFG process is described by LaBelle in "EFG—The Invention and Application to Sapphire Growth", in Journal of Crystal Growth, 50, pages 8–17 (September 1980). See also LaBelle, U.S. Pat. No. 3,591,348, LaBelle et al., U.S. Pat. Nos. 3,701,636 and 3,915,662, and other patents and articles cited in the Journal of Crystal Growth article.

Figure 5:
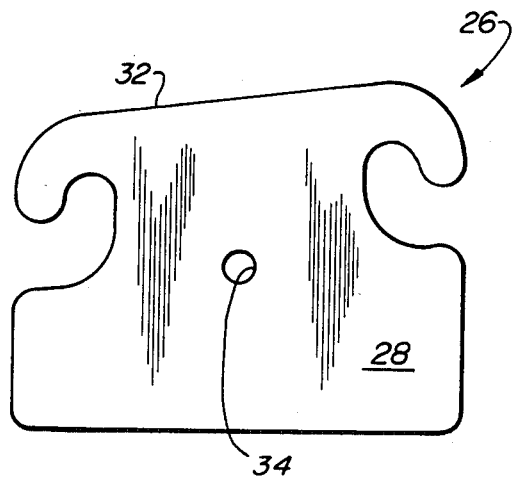
FIG. 5 is a top view of a die that is used to produce a crystalline alpha-alumina rod having a cross-sectional configuration essentially identical to the configuration of the top of said die.
Figure 6:
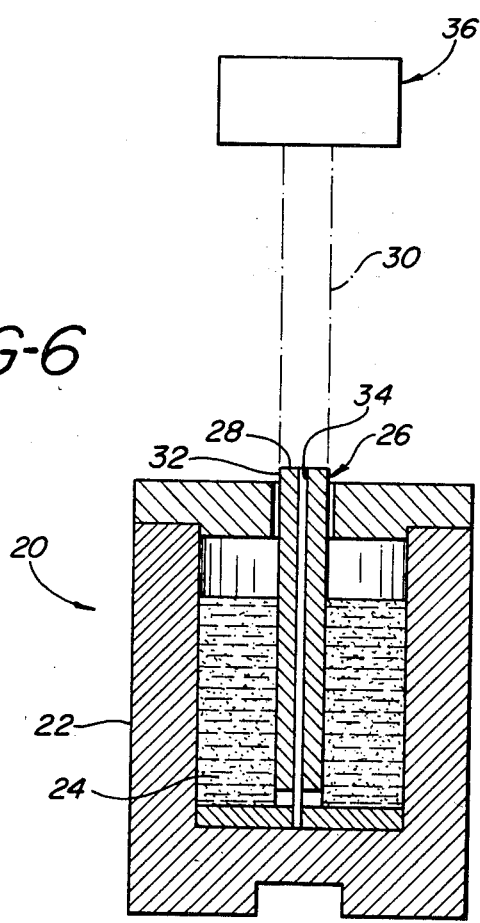
FIG. 6 is a schematic representation of apparatus for producing a crystalline alpha-alumina rod.
Figure 7:
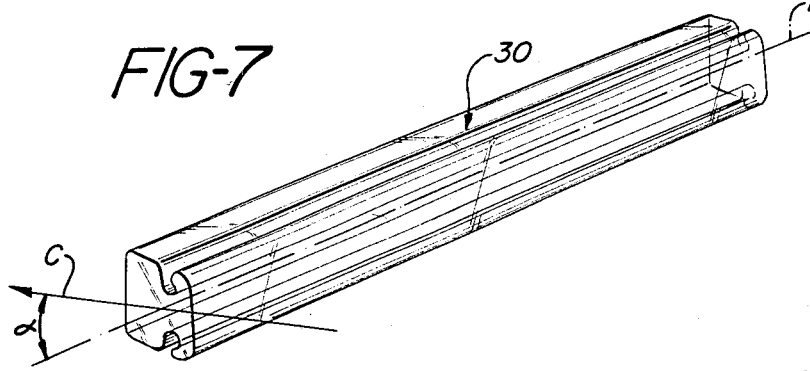
FIG. 7 is a perspective view of a crystalline alpha-alumina rod produced by the apparatus of FIG. 6.

FIG. 6 is a schematic representation of apparatus for producing a sapphire rod having a predetermined cross-sectional configuration by the EFG process. The apparatus 20 includes a crucible 22 containing molten alumina 24. A die 26 made from a suitable material such as molybdenum or iridium is positioned such that the bottom of the die 26 is immersed in the molten alumina 24, and the top of the die 26 is above the surface of the melt 24. A vertical distance above the melt 24 of up to 50 millimeters is permissible. FIG. 5 shows the top surface 28 of the die 26. The top surface 28 is smooth, flat, and has the shape of the desired configuration of the cross-section of the crystalline alpha-alumina rod 30 (shown in FIG. 7) from which the brackets are made. It is important that the side 32 of the die 26 and the top surface 28 of the die meet in a sharp 90° angle, in order to minimize imperfections in the surface of the growing rod 30. The die 26 contains a capillary passage 34 through which molten alumina 24 is drawn. The melt 24 is drawn from the crucible 22 through the capillary 34 to the top surface 28 of the die 26, where it spreads out and completely covers the said top surface 28 with a film of molten alumina. However, because molten alumina and molybdenum or iridium have the appropriate wettability relationship, the molten alumina film stops at the edge of the surface 28. Therefore, alpha-alumina crystal grown or pulled from this film of molten alumina assumes a cross-sectional configuration substantially exactly the same as the configuration of the top surface 28 of the die 26. Thus, the rod 30 (which had been started by a seed crystal, as in the Czochralski process) pulled by a pulling mechanism 36 from the film of molten alumina on the top surface 28 of the die 26 will have a cross-sectional configuration substantially identical to the configuration of the top surface 28 of the die 26.

The crystal orientation of the growing rod may prove to be important (at least economically, and perhaps also from a performance standpoint) in the practice of the invention. In the case of crystalline alpha-alumina, the crystal orientation can be defined with reference to the C axis of the crystal. (The C axis is perpendicular to the plane which contains the simplest arrangement of atoms in the crystal unit cell. Stated another way, the C axis is perpendicular to the plane which contains the $a_1$ and $a_2$ axes.) The minimum amount of strain developed in the growing crystal will occur if the C axis is found in a plane perpendicular to the longitudinal axis L of the rod 30 (see FIG. 7). This may prove to be the optimum crystal orientation in some cases. (As is known in the art, the growing crystal will assume the crystal orientation of the seed crystal.)

In other cases, however, it may be preferred to orient the C axis an angle $\alpha$ from the longitudinal axis L of the rod 30 (FIG. 7) such that the C axis is found in a conical surface formed by pivoting the C axis 360° around any point of intersection between the C axis and the longitudinal axis L, with the angle between L and the C axis being $\alpha$. In this case, the angle $\alpha$ is between 30° and 60°. The reason for orienting the crystal in this way is to minimize chipping of the crystalline alpha-alumina during machining.

Regardless of the crystal orientation of the rod 30, it is preferred to anneal the rod 30 prior to machining so as to relieve stresses in the crystal to minimize the chances of breakage during machining. A typical annealing cycle would be to heat the rod 30 from room temperature up to 1850° C. at an even rate for about 12 hours, to maintain the rod 30 at 1850° C. for 4 to 6 hours, and to then cool the rod 30 down to room temperature at an even rate for 18 to 24 hours.

Figure 8:
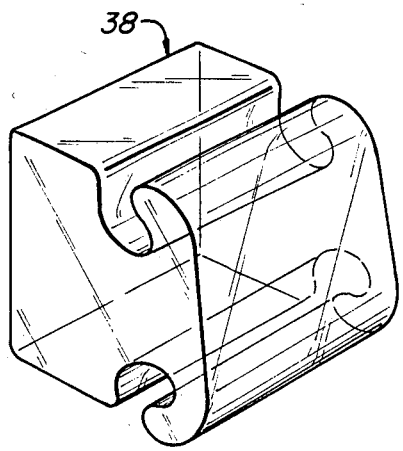
FIG. 8 is a perspective view of a bracket blank cut from the crystalline alpha-alumina rod of FIG. 7.
Figure 15:
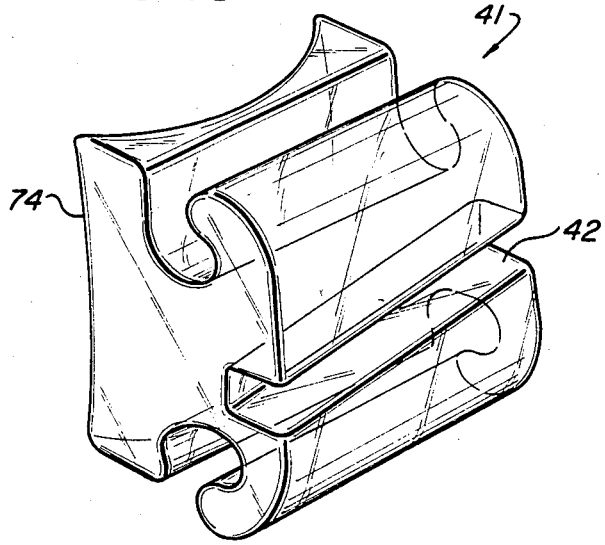
FIG. 15 is a perspective view of a "single-wing" orthodontic bracket made of crystalline alpha-alumina.

The crystalline alpha-alumina rod 30 is cut into individual blanks 38 (FIG. 8), each of which is machined into a bracket. FIGS. 1-4 are various views of an orthodontic bracket 40 made completely of crystalline alpha-alumina. The bracket 40 is made from the blank 38 by a series of cutting, grinding, and polishing steps, using known techniques for machining crystalline alpha-alumina. A diamond cutting wheel or an abrasive slurry wire saw may be used to cut out the archwire groove 42 and the "saddle" 43 of a double wing bracket (such as is shown in FIG. 1). A single wing bracket 41 is shown in FIG. 15. Edges may be beveled by grinding, and corners rounded off by polishing, by known techniques. After machining, another annealing step under the conditions suggested above is recommended to relieve stresses induced by machining.

As is shown in the drawings, the tooth contacting surface 74 of the bracket is contoured to match the curved surface of a tooth. This contour is machined by a conventional grinding procedure.

Figure 10:
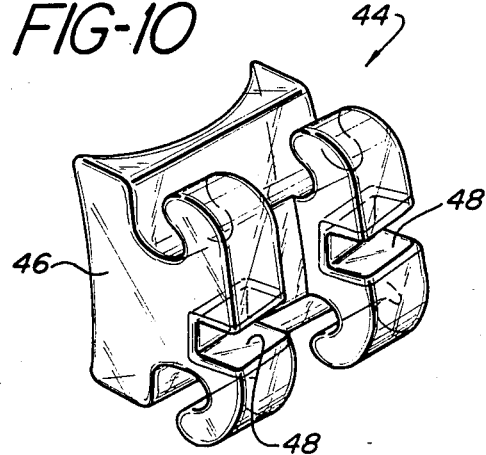
FIG. 10 is a perspective view of a plastic orthodontic bracket having a crystalline alpha-alumina liner in the archwire groove.
Figure 11:
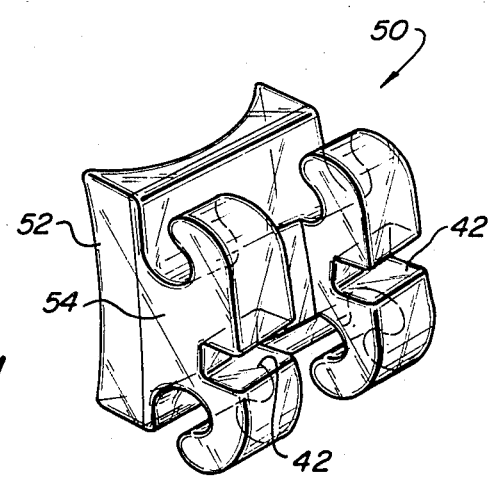
FIG. 11 is a perspective view of an orthodontic bracket having a plastic base, with the remainder of the bracket being crystalline alpha-alumina.

In alternative embodiments, the most critical load bearing portions of the bracket are made of crystalline alpha-alumina, while the remainder is made of another transparent material, such as polycarbonate or polysulfone plastic, that is less expensive, easier to work, and easier to bond to the tooth. FIG. 10 shows one such alternative embodiment, wherein the bracket 44 is made predominantly of transparent plastic 46 (e.g., polycarbonate), but wherein the archwire groove has a crystalline alpha-alumina liner 48 cemented therein by an adhesive in accordance with this invention. In another embodiment, shown in FIG. 11, the bracket 50 has a transparent plastic base 52 cemented to a crystalline alpha-alumina body 54 by an adhesive in accordance with this invention. In both of these alternative embodiments, the crystalline alpha-alumina portions can be made by a modification of the method described above, starting with a crystalline alpha-alumina rod of appropriate shape made by the EFG process.

Figure 12:
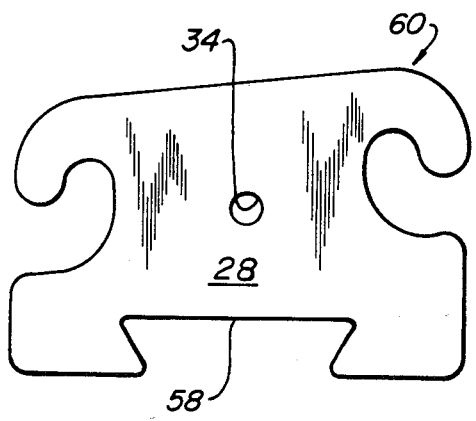
FIG. 12 is a view similar to FIG. 5, showing an alternative configuration of the top of the die.
Figure 13:
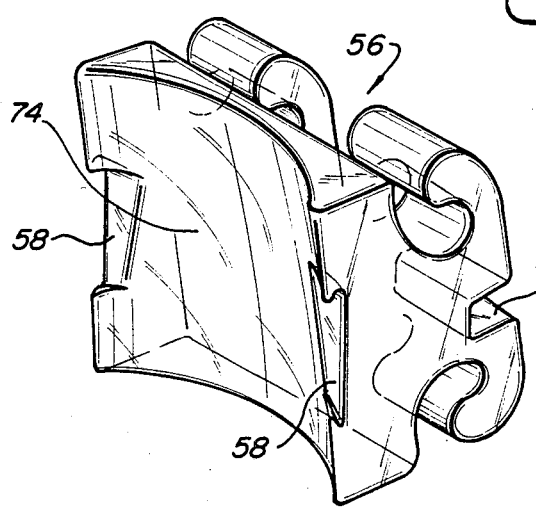
FIG. 13 is a perspective view of a crystalline alpha-alumina orthodontic bracket having a keyway in the base for the purpose of enhancing the bonding of the bracket to the tooth.
Figure 14:
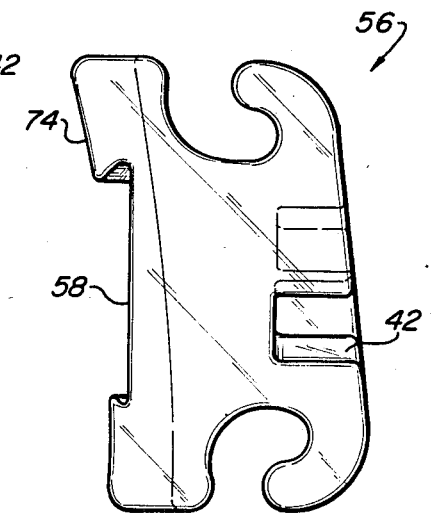
FIG. 14 is a side view of the orthodontic bracket of FIG. 13.

As was indicated above, bonding a crystalline alpha-alumina bracket to the tooth (or to a plastic base or to any other substrate) is not a straightforward matter. Crystalline alumina has a high surface energy, and many of the ordinary orthodontic cements (which are usually acrylic resins) will not adhere well enough to crystalline alpha-alumina to be useable without taking steps to enhance the adhesion. One means of enhancing the adhesion of a crystalline alpha-alumina bracket to the tooth is illustrated in FIGS. 13 and 14, in which a bracket 56 is shown that has an undercut or keyway 58 in the bottom or tooth-contacting surface 74 of the bracket 56. Orthodontic cement filling the keyway 58 will have enhanced mechanical adhesion to the bracket 56 because of the undercut portion. This bracket 56 can be made by a method analogous to that described above, starting with the EFG process using a molybdenum die 60 having a top surface shaped as shown in FIG. 12.

Figure 9:
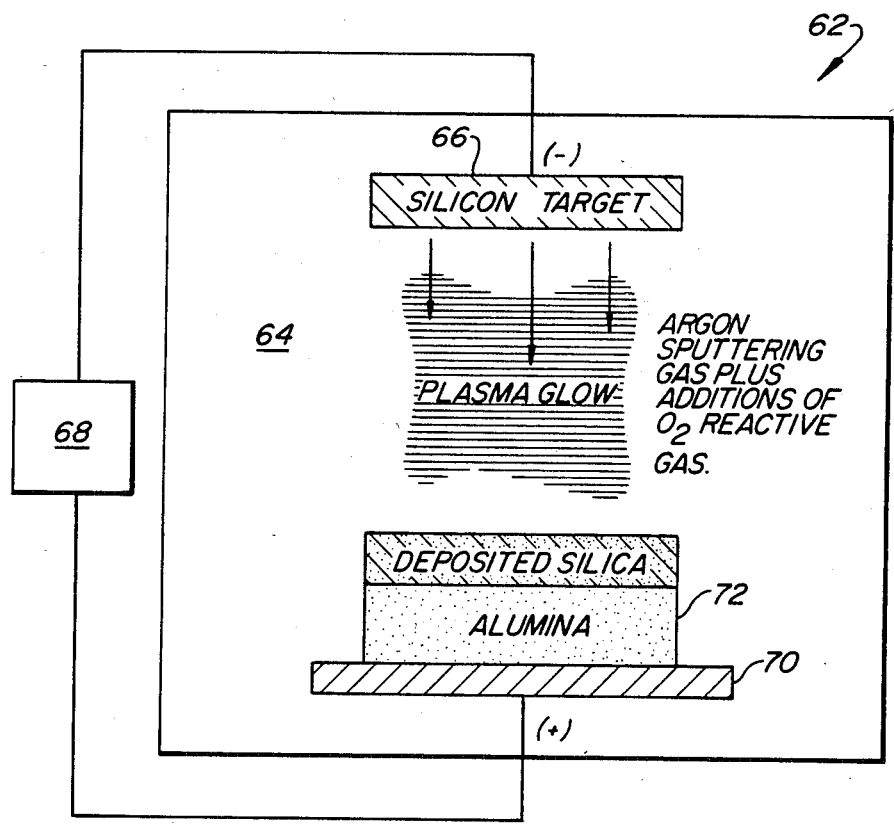
FIG. 9 is a schematic representation of apparatus for sputter coating silica on a crystalline alpha-alumina article.

This invention provides another means of enhancing the adhesion of cements such as acrylic resins to a crystalline alumina bracket by altering the surface of the crystalline alumina in such a way as to increase the strength of the adhesive bond between the crystalline alumina and the cement. It is known, for instance, that a wide variety of silicone coupling agents can be used to enhance the adhesive force between siliceous substrates and a wide variety of thermosetting plastics. However, such known technology may not be adequate in the present case, because the known coupling agents may not enhance the bond of acrylic cements to alumina to the strength required in an orthodontic application. The lack of availability of adequate coupling agents for alumina is circumvented in accordance with this invention by coating the crystalline alumina surface that is to be in contact with the cement with a thin coating (usually thinner than about 10,000 angstroms, and preferably, up to about 1,000 angstroms) of a siliceous material such as silica, and then using silicone coupling agents to enhance the bond of that surface to the cement, in a manner analogous to that which is presently known. Examples of means for coating the crystalline alumina surface with a siliceous material are cathode sputtering, plasma deposition, and electron beam evaporation, all of which are known techniques, especially in the semi-conductor arts. FIG. 9 is a schematic representation of apparatus suitable for sputter coating silica onto the surface of a crystalline alumina orthodontic bracket. The apparatus, shown generally as 62, includes a sputtering chamber 64 (which is vacuum tight), a target 66, in this case silicon metal, which is brought to cathode potential, an RF or DC power supply 68, and a plate 70 for holding the cleaned and dried substrate 72 to be coated, in which the plate 70 is brought to anode potential. A source of oxygen (not shown) introduces oxygen into the chamber 64 so that the silicon metal 66 will be converted to silicon dioxide on the substrate 72. Reactive sputtering, such as is briefly outlined here, is known. For instance, see "The Basics of Sputtering", printed in December 1980 by Materials Research Corporation, Orangeburg, N.Y. 10962.

The crystalline alumina bracket having its base surface 74 (see FIG. 2) sputter coated with silica or other siliceous material such as a glass, has a greatly enhanced affinity for silane or silicone coupling agents such as gamma-methacryloxypropyltrimethoxysilane, and by using such coupling agents the adhesion of the bracket to acrylic orthodontic cements is greatly enhanced. This is illustrated in the Examples, below:

EXAMPLE 1 and CONTROL EXAMPLES 1–6

The purpose of the experiments described below was to measure the shear strength between various materials and a plug of adhesive. The experiments were carried out by inserting a crystalline alpha-alumina 0.2 inch diameter rod (or a steel rod, to simulate a steel orthodontic bracket) treated in various ways into the end of a short length of "Tygon" laboratory tubing, and then building up a plug of an acrylic orthodontic cement on the end of the rod by tamping it into the tubing against the end of the rod. After the cement hardened, the shear strength between the rod and the cement was measured by the test procedure described below.

The acrylic orthodontic cement used was a two-paste formulation having the following composition:

| Component | Weight Percent Universal | Catalyst |
|---|---|---|
| 2,2-bis[4-(3-methacryloxy-2-hydroxypropoxy)phenyl]propane ("Bis-GMA") | 12.60 | 12.80 |
| Bisphenol-A Dimethacrylate | 1.40 | 1.42 |
| Triethyleneglycol Dimethacrylate | 6.09 | 6.09 |
| 2-Hydroxy-4-methoxybenzophenone | 0.20 | 0.20 |
| Butylated hydroxytoluene | 0.01 | 0.03 |
| N,N—di(2-hydroxethyl)-p-toluidine | 0.50 | — |
| Benzoyl Peroxide | — | 0.40 |
| Quartz powder-silane treated | 75.00 | 75.86 |
| Fumed Colloidal Silica | 3.20 | 3.20 |
| Pigments | 1.00 | — |

Approximately equal quantities of the two pastes are mixed just before use, and a total of about 0.5 gram of the mixed cement is spatulated into the open end of the tubing and tamped against the end of the rod, to build up a short plug of cement. After the cement has hardened (within 3 to 5 minutes), the tubing is cut away and the sample is placed in water at 37° C. for 48 hours, after which it is tested.

An Instron Testing Machine is used. The sample is placed on its side in a "V" shaped steel block and is clamped tightly therein. In this test, the cured cement is sheared off at the rod/cement interface with a steel blade secured to the cross head of the Instron machine. The blade was positioned as closely as possible to the interface, about ½ to 1 millimeter from the interface on the cement side thereof, and the shearing force exerted at the interface was determined using a cross head speed of 0.05 inch/minute.

The various samples tested were the following:

Control 1—Mesh bonded stainless steel rod. The rod was stainless steel having an 80 mesh, square weave metal wire vacuum brazed onto the end of the rod.

Control 2—Crystalline alpha-alumina rod, etched in sulfuric acid (20% aqueous) by boiling for 2 minutes (all of the crystalline alpha-alumina rods were etched in sulfuric acid to thoroughly clean them prior to treatment, unless otherwise specified). This rod had no further treatment.

Control 3—Crystalline alpha-alumina rod, treated with a 1% solution in ethanol of Z-6032 silane from Dow Corning. This silane has the following structure:

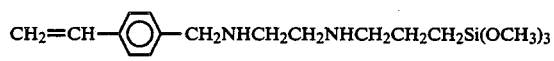

Control 4—Crystalline alpha-alumina rod, treated with a 1% ethanol solution of gamma-methacryloxypropyltrimethoxysilane (A-174).

Control 5—Crystalline alpha-alumina rod, treated with a 1% ethanol solution (based on weight of silane) of an epoxy/silane primer prepared as follows:

6.13 grams of A-1100 silane (gamma-aminopropyltriethoxysilane) and 19.3 grams of the diglycidyl diether of bisphenol-A were added to a reaction vessel and heated to 60° C. 4.77 Grams of methacrylic acid was dripped into the mixture over a period of three hours. When the mixture became quite viscous, ethanol was added. At the conclusion of the methacrylic acid addition, more ethanol was added to reach a 1% solution, based on the silane.

Control 6—Crystalline alpha-alumina rod treated with a Bis-GMA/silane primer that was prepared in the following manner:

91.9 millequivalents of Bis-GMA was reacted with 22.85 millimoles of A-1100 silane in the presence of 5 drops of acetic acid, in ethanol solution in a Michael addition. The reaction product was applied to the sapphire in a 1% ethanol solution.

Example 1—Crystalline alpha-alumina rod coated with a layer of silica about 10,000 Angstroms thick by electron beam evaporation. (This rod was not acid-etched, since the electron beam treatment cleans the surface adequately). Prior to treating the silica-coated rod with a silane coupling agent, the coated rod is heated in air at 350° C. for one hour. This converts the silica surface to a form that has a greater affinity for the silane. (It appears that silanol groups are thereby formed, the moisture content of air being sufficient to promote their formation.) Heating in ethylene chloride also has the same effect, for reasons that are not clear. The silica coated rod was treated with a ½% ethanol solution of A-174 silane by spraying, followed by air drying. The silane is then hydrolyzed by immersion in water for one hour at room temperature.

The results of the shear tests are displayed below in Table I:

TABLE I

| Sample | Shear Strength, Psi |
|---|---|
| Control 1 | 1630 (650) |

TABLE I-continued

| Sample | Shear Strength, Psi |
| --- | --- |
| Control 2 | 570 (310) |
| Control 3 | 1010 (420) |
| Control 4 | 700 (515) |
| Control 5 | 1170 (320) |
| Control 6 | 970 (33) |
| Example 1 | 1420 (165) |

The values in parentheses were the standard deviations. Three specimens of each sample were tested. The value obtained for Control 1, the mesh bonded steel rod, is considered to be approximate maximum obtainable with the cement tested. In Control 1, the cement itself failed, rather than the interface.

As the foregoing experiment indicates, the addition of a thin, adherent coating of a siliceous material (in this case, silica) to the surface of crystalline alumina enables one to obtain a strong adhesive bond between crystalline alumina and adhesives. In the preferred way of practising the invention, a silane coupling agent is used to enhance the bond between the siliceous coating and the adhesive. The type of silane that is used is dependent upon the nature of the adhesive, as is known in the art.

For instance, when an acrylic resin is used as the adhesive (or, indeed, any adhesive that cures by polymerization of an ethylenic double bond), the silane (e.g., A-174) will ordinarily contain an ethylenic double bond that interacts with the resin. If an epoxy adhesive is used, the silane (e.g., A-1100) will usually contain an amino group, preferably a primary amino group, which group will interact with the polymerizing epoxy resin. The principles of selecting a coupling agent to enhance the bond between a siliceous material and an adhesive are known, and the known principles are applicable here.

The invention has been described most particularly with respect to the use of crystalline alpha-alumina (sapphire) as the material from which orthdontic brackets are made. However, other crystalline alumina materials can be used in the invention. The limiting requirements for an orthodontic bracket are adequate modulus of rupture (i.e., greater than about 35,000 psi, which is the yield strength of the steel that is currently used for most orthodontic brackets), and sufficient transparency that the natural tooth color can be seen through the bracket. Other crystalline alumina materials that can be used include yttrium aluminum garnet, magnesium aluminum spinel, and alpha-alumina in which a small percentage of the aluminum atoms has been replaced with other elements to impart color and/or fluorescence to the crystal. For instance, fluorescence can be imparted to the crystal by the addition of small amounts (e.g., less than 1 mole percent) of terbium oxide or cerium oxide to the aluminum oxide.

The invention is also not limited to orthodontic brackets. It is applicable to any composite wherein a crystalline alumina article is to be bonded to another article.

The siliceous coating on the alumina is preferably silica, but can also be other siliceous materials such as glasses that contain significant amounts, usually at least 50 mole percent, of silica. Other materials that can be present in the siliceous material include alkali metal oxides, alkaline earth metal oxides, boron oxide, lead oxide, alumina, rare earth metal oxides (to impart fluorescence), and the like.

What is claimed:

1. A composite comprising a crystalline alumina article adhesively bonded to a substrate, wherein at least a portion of the surface of said article that is adhesively bonded to said substrate comprises crystalline alumina having a thin adherent coating of a siliceous material, wherein said siliceous material consists essentially of silica or a glass containing at least 50 mol percent silica.

2. The composite of claim 1 wherein the adhesive bond between said coating of a siliceous material and the adhesive bonding said article to said substrate is enhanced by a silane coupling agent.

3. The composite of claim 1 or 2 wherein said crystalline alumina is crystalline alpha-alumina.

4. The composite of claim 1 or 2 wherein said siliceous material is silica.

5. The composite of claim 3 wherein said siliceous material is silica.

6. The composite of claim 1 or 2 wherein said article is an orthodontic bracket comprising a base member including a tooth contacting surface and a body member extending from said base member, said body member including walls defining an archwire groove.

7. The composite of claim 3 wherein said article is an orthodontic bracket comprising a base member including a tooth contacting surface and a body member extending from said base member, said body member including walls defining an archwire groove.

8. The composite of claim 2 wherein said article is an orthodontic bracket comprising a base member including a tooth contacting surface and a body member extending from said base member, said body member including walls defining an archwire groove.

9. The composite of claim 8 wherein said composite comprises an orthodontic bracket.

10. The composite of claim 2 wherein the adhesive is an epoxy resin and the silane coupling agent contains an amino group.

11. A method of producing a composite which comprises the steps of coating at least a portion of the surface of a crystalline alumina article with a thin adherent coating of a siliceous material, and then bonding said article to a substrate by adhesively bonding said surface having the siliceous coating to the substrate using an adhesive that has an adhesive affinity for said siliceous coating.

12. The method of claim 11 wherein said siliceous material is silica.

13. The method of claim 11 or 12 wherein the crystalline alumina is crystalline alpha-alumina.

14. The method of claim 11 or 12 wherein the adhesive bond between said adhesive and said siliceous coating is enhanced by the use of a silane coupling agent.

15. The method of claim 14 wherein the adhesive is an acrylic material and the silane coupling agent contains ethylenic unsaturation.

16. The method of claim 11 or 12 wherein said article is an orthodontic bracket comprising a base member including a tooth contacting surface and a body member extending from said base member, said body member including walls defining an archwire groove.

17. The method of claim 13 wherein said article is an orthodontic bracket comprising a base member including a tooth contacting surface and a body member extending from said base member, said body member including walls defining an archwire groove.

18. The method of claim 14 wherein said article is an orthodontic bracket comprising a base member including a tooth contacting surface and a body member extending from said base member, said body member including walls defining an archwire groove.

19. The method of claim 15 wherein said article is an orthodontic bracket comprising a base member including a tooth contacting surface and a body member extending from said base member, said body member including walls defining an archwire groove.

* * * * *